United States Patent [19]

Hakky

[11] Patent Number: 4,908,207
[45] Date of Patent: * Mar. 13, 1990

[54] METHOD OF TREATMENT OF A PERSON HAVING A COMPROMISED HUMAN IMMUNE SYSTEM

[76] Inventor: Said I. Hakky, 8547 Merrimoor Blvd. East, Largo, Fla. 33543-2536

[*] Notice: The portion of the term of this patent subsequent to May 2, 2006 has been disclaimed.

[21] Appl. No.: 43,002

[22] Filed: Apr. 27, 1987

[51] Int. Cl.$^4$ .................. A61K 35/78; A61K 31/34; A61K 31/12; A61K 31/045
[52] U.S. Cl. ................ 424/195.1; 514/468; 514/691; 514/729; 514/864
[58] Field of Search ............ 424/195.1; 514/468, 514/691, 729, 864

[56] References Cited

U.S. PATENT DOCUMENTS 4,569,843  2/1986  Kim ........................ 424/195.1

OTHER PUBLICATIONS

Chem. Abst. 88: 86013h, 1978.
Chem. Abst. 88: 51025m, 1978.
Chem. Abst. 93: 253516ln, 1980.

*Primary Examiner*—John W. Rollins
*Attorney, Agent, or Firm*—Caesar, Rivise, Bernstein, Cohen & Pokotilow, Ltd.

[57] ABSTRACT

A method of producing a composition for use in the treatment of a compromised human immune system is described. The active ingredient in the ingredient in the composition is a mixture of terpenoids derived from an extract of the tubers of the plant Cyperus rotundus Linn and is administered orally to a patient having a compromised immune system. The prepared extract can be in a powder form or in a volatile oil.

The composition can also be administered parenterally. In clinical trials on humans a flavour enchanced composition derived from an agneous-based paste resulted in significant therapeutic benefit with no side effects.

The production of the composition and method of a human patient having a compromised immune system is also described.

3 Claims, No Drawings

METHOD OF TREATMENT OF A PERSON HAVING A COMPROMISED HUMAN IMMUNE SYSTEM

BACKGROUND OF THE INVENTION

This invention relates to the use of compounds found in, or prepared or extracted from plant sources in the fabrication of a pharmaceutically active material for enhancing the immune system and particularly, but not exclusively, restoring compromised immune systems.

Insulin-dependent mellitus (IDDM) is a form of diabetes in which the patient's glucose metabolism can only be controlled by injection of insulin from two to four times a day as a permanent ongoing medication. Some diabetics are known to have a compromised immune system and tend to be more susceptible to disease than non-diabetics. Because of their weak conditions it is important to be able to restore the immune system to "normal" activity to fight or prevent disease and ensure patient well being.

Certain remedies have been proposed to support the immune systems such as antibiotics, but their use is not widespread, nor successful, they are just supportive.

The present invention, however, in one aspect sets out to provide such a material of vegetable origin and based on the plant Cyperus rotundus Linn which is a pantropic species grown in some oriental countries and also widely occurring as a weed, the English name of which is "Nut Grass", and the French "Souchet frond". It is a glabrous slender sedge, with an elongate underground stem, filiform with ovate-oblong tubers. The culms are slender, triquetous, 60–150 cm-tall, and densely leafy at the base. The rays of the umbels vary from 3 to 9; they are unequal and may be simple or branching.

The plant has an elaborate underground system of stolons, tubers and roots. The tubers (with which this invention is primarily concerned, and which are also referred to herein as rhizomes) are succulent and white when young but when mature turn black.

It is well known to use the tubers for a wide range of medicinal purposes. Thus, the roots have been reported as being emmenagogue, sedative, antispasmodic, demulcent and hemostatic. Uterine disorders (amenorrhea, menorrhagia) and childbrith problems are also counteracted. It is stated moreover to be tonic, stomachic, expectorant, diuretic, antifebrile, decongestant and antirheumatic, among a long list of other qualities, and to relieve headaches or external pains, e.g. toothaches, whitlows. Hitherto, however, this well documented and ancient remedy has not been suggested as, or in, a food or medicine active for enhancing the immune system or for restoring a compromised immune system.

In one aspect the invention consists in the use of a material found in, or extracted or prepared from the plant Cyperus rotundus Linn in the preparation of a medicine or foodstuff for the treatment of patients having a compromised immune system, and of patients having insulin-dependent diabetes mellitus.

Preferably, the material is an ingestible powder, and most preferably it is prepared by drying and grinding tubers of the plant, especially the mature tubers.

The dried powder material itself is active in enhancing the immune system, and in accordance with the invention it is used always in the preparation of the medicine or foodstuff together with a proportion (preferably a minor proportion) of the dried and powdered gum of Pistacia lentiscus Linn which is used as a flavour enhancer only.

Another aspect of the invention consists in the use of the extracted violatile oil component of the tubers of Cyperus rotundus Linn in the preparation of a pharmaceutically active material for the treatment of deficient immune systems.

Preferably the extraction is carried out by steam distillation of the tubers in a known procedure, yielding up to 2% of a violatile oil. Extract compounds vary with the origin and subspecies of the Cyperus rotundus, but the oil appears to be essentially a mixture of 10, 20 or more terpenoids, among which have been identified a sesquiterpene known x-cyperone (up to 50%) and significant amounts of cyperene, a tricyclic sesquiterpend ($C_{15}H_{24}$) and cyperol, a tricyclic alcohol, $C_{15}H_{24}O$.

Another aspect of the invention consists in a method of treatment of deficient immune systems consisting of orally administering a pharmaceutically effective amount of a compound having at least one terpenoid found in the plant Cyperus rotundus Linn.

While it is possible for the composition defined above or, where appropriate pharmaceutically acceptable salts thereof (hereinafter referred to as the "active compounds") to be administered as the raw chemical it is preferred that the active compound is presented in the form of a pharmaceutical composition.

In a further aspect of the invention there is therefore provided a pharmaceutical formulation comprising the active compound together with a pharmaceutically acceptable carrier therefor. The carrier must be "acceptable" in the sense of being compatible with the other ingredients of the formulation and not deleterious to the receipient thereof. Such carriers are solid, liquid or gaseous materials recommended for the purpose of administering the medicament.

These pharmaceutical compositions may be administered orally or parenterally (including subsutaneous, intramuscular and intravenous injection) or as a suppository or pessary. It is preferred that the compositions are administered orally. The terms formulation and composition are used synonomously.

For oral administration the pharmaceutical compositions may be presented as a draught in water or in a syrup, in capsules, cachets, boluses or tablets, as an aqueous or oleaginous solution or suspension or in suspension in a syrup, such suspension optionally including suspending agents or as an oil-in-water or water-in-oil emulsion. Where desirable or necessary flavouring, sweetening, preserving, thickening or emulsifying agents may be included in the formulation.

Tablets may contain the active compound as a powder or granules optionally mixed with binders, lubricants, inert diluents or surface-active or dispensing which are useful in such formulations.

All the above formulations are produced by processes which comprise bringing into association the active compound and one or more carriers.

The invention will be further described with reference to the following examples of preparation, in vitro testing and clinical test.

EXAMPLE I

Tubers of Cyperus rotundus Linn were dried to constant weight in a vacuum oven at room temperature and powdered for extraction.

Extractions

A. Aqueous Extract. 50 gms. of powder was boiled with water for four hours. The mixture was filtered and the aqueous extract was evaporated to dryness on a rotary evaporator below 45 C. The extract yielded 3.9 grams of solid—7.6% w/w of original plant material.

B. Ethanolic Extract. 20 gms of powder was extracted by maceration at room temperature for one week with redistilled alcohol. The mixture was filtered and evaporated as before. The extract yielded 0.33 gms of solid—6.5% w/w of original plant material.

C. Preparation of volatile oil. 50 gms of powder was steam distilled in the B.P. "determination of volatile oil" apparatus. The pure oil separated from the condensed steam in the side arm. The water was run off and rejected and the oil collected in a glass vial. The yield was 1 ml per 50 grams of power—2% V/W.

Thin-layer —Chromatographic (TLC) Analysis of Oil

The oil was subject to micro-analysis on silica gel precoated/aluminium plates using a toluene/ethyl acetate as solvent and visulised with 5% vanillin in concentrated $H_2SO_4$. It was a complex mixture of terpenoids, containing at least 15 separate compounds. These substances gave a colour spectrum containing blue, purple, red, orange and yellow colours when reacted with the spray reagent to indicate the composition and type of oils.

Clinical Test

A powder comprising Cyperus rotundus Linn tubers dried and powdered (42 g), Pistacia lentiscus Linn, gum dried and powdered was mixed with sufficient water to form a paste. 5 ml of the paste was administered four times daily, after meals, to a 7 year old boy weighing about 25 kg suffering from IDDM and treated with two injections daily of 8 units of insulin, resulting in a dosage of about 1-2 grams Cyperus powder/kg body weight/day. After six weeks of such treatment a flattening of the blood glucose curve was observed and the rate of injection of insulin was halved without adverse effect. It was observed that the insulin requirement varied according to the level of physical exercise of the patient. When no physical exercise was undertaken the reduction of 70% whereas with 1 to 2 active exercise per day, such as swimming, running or football the reduction reached 100%. After one year of clinical trials excluding Pistacia and Iris no ill effects or change was observed. It was concluded that Cyperus rotundus Linn was the active ingredient. Further clinical trials were carried out with Cyperus only and the results were consistent with laboratory testing.

It is known that some diabetics have a compromised immune system, even though once they are controlled, their immune system can become more or less normal for the age. However, it was shown over the 18 months period that the boy of 9 year of age became virtually immune to all current viral or bacterial infections which his close members of his family had over such a period. All members of the family had some form of viral respiratory infection at least 3 times in that period while the 9 year old diabetic showed trivial symptoms and very short periods of illness. Such enhanced immune system can be atributed to cellular as well as serum factors. Cellular (i.e. lymphocyte mitogenesis test) increase may explain this high immune system status.

The method of treatment using the product and the actual product for use is original, novel, inventive and useful. Although the exact mechanism of behaviour of the active ingredient is not fully understood it is believed that the sensitivity and number of leucocytes are enhanced.

It will be understood that various modifications may be made to the examples and compositions hereinbefore described without departing from the scope of the invetnion. For example, the active ingredient may be terpenoids derived from any suitable parent source other than the tubers of the plant Cyperus rotundus Linn. Also, such an active ingredient may be derived synthetically and used to enhance the immune system in the same way as with the plant derived active ingredient. Accordingly, such alternative compositions should also be within the scope of the invention.

Without further elaboration the foregoing will so fully illustrate my invention that others may, by applying current or future knowledge, adopt the same for use under various conditions of service.

I claim:

1. A method of treatment of a person having a compromised human immune system comprising the steps of administering to said person a therapeutic amount of a composition having at least one terpenoid found in the plant Cyperus rotundus Linn in a pharmaceutically effective amount in a pharmaceutically acceptable carrier to such person.

2. A method of treatment as claimed in claim 1 including the step of administering said composition orally.

3. A method of treatment as claimed in claim 1 including the steps of monitoring the glucose levels of the diabetic and correlating the glucose levels with the dosage of the composition administered.

* * * * *